United States Patent [19]

Bussemeier et al.

[11] Patent Number: 4,564,642

[45] Date of Patent: Jan. 14, 1986

[54] PROCESS FOR THE MANUFACTURE OF UNSATURATED HYDROCARBONS

[75] Inventors: Bernd Bussemeier, Mulheim; Carl D. Frohning; Gerhardt Horn, both of Oberhausen; Werner Kluy, Bochum-Stiepel, all of Fed. Rep. of Germany

[73] Assignee: Ruhrchemie Aktiengesellschaft, Fed. Rep. of Germany

[21] Appl. No.: 321,086

[22] Filed: Nov. 13, 1981

Related U.S. Application Data

[63] Continuation of Ser. No. 122,744, Feb. 19, 1980, abandoned, which is a continuation of Ser. No. 963,149, Nov. 22, 1978, abandoned, which is a continuation of Ser. No. 832,722, Sep. 12, 1977, abandoned, which is a continuation of Ser. No. 711,857, Aug. 6, 1976, abandoned.

[30] Foreign Application Priority Data

Aug. 16, 1975 [DE] Fed. Rep. of Germany ....... 2536488

[51] Int. Cl.$^4$ ................................................ C07C 1/04
[52] U.S. Cl. .................................... 518/717; 518/705; 518/721
[58] Field of Search ........................ 518/717, 721, 715

[56] References Cited

U.S. PATENT DOCUMENTS

| | | |
|---|---|---|
| 2,231,990 | 2/1941 | Dreyfus . |
| 2,271,259 | 1/1942 | Herbert . |
| 2,279,052 | 4/1942 | Michael et al. . |
| 2,289,731 | 7/1942 | Roden et al. . |
| 2,318,602 | 5/1943 | Duftschmidt et al. . |
| 2,455,419 | 12/1948 | Johnson . |
| 2,615,911 | 10/1952 | Williams . |
| 2,666,077 | 1/1954 | McGrath . |
| 2,700,676 | 1/1955 | McGrath . |
| 2,960,518 | 11/1960 | Peters . |
| 4,151,190 | 4/1979 | Murcheson . |

FOREIGN PATENT DOCUMENTS 922883 1/1955 Fed. Rep. of Germany .

Primary Examiner—Howard T. Mars
Attorney, Agent, or Firm—Jordan B. Bierman

[57] ABSTRACT

A process for the production of unsaturated hydrocarbons by the catalytic hydrogenation of carbon monoxide is disclosed wherein the reaction takes place in the presence of a catalyst containing an oxide of a first metal selected from the transition metals of Group IV and a second metal selected from Group VIII of the periodic table. The reaction takes place at a reaction temperature of between about 250° C. and 350° C. and a reaction pressure of between about 10 and 30 bar.

9 Claims, No Drawings

PROCESS FOR THE MANUFACTURE OF UNSATURATED HYDROCARBONS

This application is a continuation of application Ser. No. 122,744, filed Feb. 19, 1980 now abandoned, which is a continuation of application Ser. No. 963,149, filed Nov. 22, 1978 now abandoned, which is a continuation of application Ser. No. 832,722, filed Sept. 12, 1977 now abandoned, which is a continuation of application Ser. No. 711,857, filed Aug. 6, 1976 now abandoned and which claims the priority of German application No. P 25 36 488.9, filed Aug. 16, 1975.

According to the present invention, high yields of unsaturated hydrocarbons, especially gaseous olefins, are obtained by the catalytic hydrogenation of carbon monoxide in the presence of particularly selected catalysts. The catalysts employed contain the oxides of the transition metals of Group IV of the periodic table in combination with metals of Group VIII of the periodic table. In addition, the present invention also provides for the addition of activators and carriers.

Various prior art methods for the production of unsaturated hydrocarbons have been characterized as requiring high temperature reaction systems. For example, a process is described in DT-PS No. 922 883 wherein carbon monoxide is reacted with hydrogen in the presence of finely divided fused iron catalysts. During this process, the catalysts are periodically or continuously removed from the reaction chamber, regenerated, reduced and recycled. The reaction is carried out at a normal or slightly increased pressure and at temperatures above approximately 450° C., preferably between about 470° C. and 600° C.

In another process, described in DT-PS No. 896 338, unsaturated gaseous hydrocarbons are obtained by reacting carbon monoxide and hydrogen in the presence of stable oxides of the metals of Group II–VII of the periodic table. The reaction takes place at approximately atmospheric pressure and at temperatures above 520° C.

The high reaction temperatures employed in the above-described reactions result in a conversion of carbon monoxide to carbon in accordance with the Bouduard equilibrium. The resulting carbon is deposited on the catalyst surface which results in the deactivation of the catalyst. This further leads to a rupture of the catalyst structure, whereby the life of the catalyst is considerably reduced.

In order to overcome the problems associated with high reaction temperatures, the prior art publication DT-AS No. 1 271 098 discloses a catalyst consisting of at least 98% by weight of a carrier and from 0.3 to 2% by weight of cobalt, nickel or platinum. This catalyst is employed in a reaction having a throughput rate of 2,500 to 3,000 liters of gas per liter of catalyst per hour. The reaction temperature is held between 300° C. and 450° C. with a reaction pressure of between 130 and 200 mm of mercury. While this process is excellent for the selective preparation of lower gaseous olefins, it is unsatisfactory because of its characteristically low yields. The average yield of this process is within the range of 10 and 20%.

There are several factors which contribute to the low yield of lower gaseous olefins produced by the catalytic hydrogenation of carbon monoxide. The conversion of carbon monoxide into hydrocarbons depends to a large extent on the partial pressure of the hydrogen. Generally, the greater the partial pressure of hydrogen, the higher the yield of hydrocarbons. However, as the partial pressure of hydrogen increases, there is a corresponding increase in the hydrogenation of primarily found olefins. In addition, there is a secondary conversion, described by the below-mentioned formula, wherein carbon dioxide is formed.

$$H_2O + CO \rightleftharpoons H_2 + CO_2$$

According to these reactions, a significant amount of carbon monoxide is lost and does not form the intended gaseous olefins. Therefore, one must seek selective catalysts which maximize the conversion of carbon monoxide to unsaturated hydrocarbons, and, at the same time, minimize the further hydrogenation of the desired product. In addition, it is necessary to minimize the loss of carbon monoxide by preventing the formation of carbon dioxide.

In order to overcome the problems associated with the prior art, the present inventors have determined that high yields of unsaturated hydrocarbons, especially gaseous olefins, can be obtained by the catalytic hydrogenation of carbon monoxide in the presence of particularly selected catalysts containing an oxide of a transition metal of Group IV and a metal of Group VIII of the periodic table. Instead of the oxides of the Group IV transition metals, it is possible to use a compound containing one of the metals which decomposes under the conditions of the reaction to form a stable oxide of the Group IV transition metal.

The preferred transition metals of Group IV include titanium, zirconium, hafnium, and thorium. The most preferred metals of this group are titanium and thorium. Iron and cobalt are the most preferred metals selected from Group VIII of the periodic table.

The catalytic hydrogenation of carbon monoxide in the presence of the present catalysts, takes place at a reaction temperature of between about 250° C. and 350° C. and a reaction pressure of between about 10 and 30 bar.

The preparation of the present catalysts takes place in a known manner. For example, the catalyst can be prepared by precipitating the components from their respective aqueous solutions using suitable precipitating agents (e.g., alkali metal carbonates). Another process involves mixing the components and then homogenizing the mixture and forming the desired catalyst by mechanical means. Finally, the catalyst can also be prepared by sintering the component parts.

In order to increase the activity of the present catalysts, it is desirable to add activators such as, for example, alkali metal carbonates or alkali metal oxides, magnesium oxide or zinc oxide. Additionally, carriers can preferably be added to the catalyst. Examples of these carriers include natural or synthetic silicic acid, kieselguhr, diatomaceous earth, aluminum oxixe, aluminum oxide hydrate, synthetic or natural silicates (e.g., magnesium silicate, aluminum silicate or pumice).

The weight ratio of the metals of Group VIII and the metals of Group IV is preferably between about 10:1 and 2:1. If a carrier is used in the present process, it is desirable to add no more than 50% by weight of the carrier material based on the total weight of the catalyst. The most preferred catalyst of the present invention contains 100 parts by weight of iron, 10 to 50 parts by weight of titanium, 3 to 5 parts by weight of potassium oxide and 5 to 15 parts by weight of zinc oxide.

The present process advantageously calls for reducing the catalyst prior to its reaction with carbon monoxide and hydrogen. This reduction step should be carried out at a temperature of between about 350° C. and 520° C. and a pressure of approximately 1 bar. The catalysts are generally used in a fixed bed. However, they can be finally divided in which case they are displaced by the vortex formed by the gas flowing through the reaction chamber. The catalyst can be continuously or intermittently removed from the reaction vessel in order to effect regeneration. They can be freed from adhering impurities in a special vessel by burning them in the presence of air followed by reducing them in a known manner.

The new process can be conducted by passing a mixture of carbon monoxide and hydrogen over the catalyst in the reaction chamber at a temperature of approximately 300° C. It is desirable to have the carbon monoxide/hydrogen volume ratio in the range of between about 2:1 to 1:2. Gas mixtures are preferably employed in which the volume of carbon monoxide is slightly greater than that of hydrogen. The gas mixture, after the removal of unsaturated gaseous hydrocarbons, is at least partly recycled into the reaction chamber.

According to the present invention, the total conversion of carbon monoxide and hydrogen is approximately 80 to 90%. Additionally, 65 to 75% of the reaction products produced are the highly desirable $C_2$ to $C_4$ olefins.

The following example is for illustrative purposes only and is not meant to limit the present invention in any manner.

EXAMPLE 1

Iron oxide (e.g., $Fe_2O_3$, $Fe_3O_4$), titanium oxide ($TiO_2$), zinc oxide and potassium carbonate were mixed to obtain a mixture having 100 parts by weight of iron, 25 parts by weight of titanium, 10 parts by weight of zinc oxide and 4 parts by weight of potassium oxide. The mixture was then homogenized. The catalyst obtained after forming and sintering the mixture at 1,050° C. was finally reduced for several hours at 500° C.

A 30 cm high layer of the catalyst was loaded into an experimental oven having a length of 1 m and an inside diameter of 10 mm. An electrical heater was employed to heat the reactor to the desired temperature. A carbon monoxide/hydrogen mixture (mole ratio 1:1), having a rate of flow of 500 Nl/liter of catalyst per hour, was introduced at a temperature of 340° C. and a pressure of 10 bar. The conversion of carbon monoxide and hydrogen was determined to be 87% with a yield of 178 g. The reaction product contained:

|  |  |  |
|---|---|---|
| $C_2H_4$ | 33.4 | wt. % |
| $C_3H_6$ | 21.3 | " |
| $C_4H_8$ | 19.9 | " |
| $C_2$–$C_4$ (saturated) | A 9.9 | " |
| Total | 84.5 | wt. % |

Additionally, 10.1% by weight of methane was also obtained. The remaining products consisted of hydrocarbons having more than 4 carbon atoms

What we claim is:

1. A process for the production of unsaturated hydrocarbons having 2 to 4 carbon atoms by the catalytic hydrogenation of carbon monoxide which comprises the steps of reacting hydrogen and carbon monoxide in a reaction vessel at a reaction temperature of between about 250° C. and 350° C. and a reaction pressure of between about 10 and 20 bar in the presence of a catalyst consisting essentially of iron, an oxide of titanium, zinc oxide and potassium oxide, wherein the weight ratio of said iron to said titanium is between about 10:1 and 2:1.

2. The process of claim 1 wherein said catalyst further contains a carrier in an amount of not more than 50 percent by weight of said catalyst.

3. The process of claim 1 wherein said catalyst consists essentially of 100 parts by weight of iron, 10 to 50 parts by weight of titanium, 3 to 5 parts by weight of potassium oxide and 5 to 15 parts by weight of zinc oxide.

4. The process of claim 1 further comprising:
   (a) continuously or intermittently removing said catalyst from the reaction vessel,
   (b) burning said catalyst in the presence of air whereby impurities are removed,
   (c) reducing said catalyst, and
   (d) returning said catalyst to the reaction vessel.

5. The process of claim 1 wherein the mole ratio of said carbon monoxide and said hydrogen is between about 2:1 and 1:2.

6. The process of claim 5 wherein said ratio is slightly greater than 1:1.

7. The process of claim 1 further comprising:
   (a) removing said unsaturated hydrocarbons, and
   (b) recycling the unreacted carbon monoxide and hydrogen to said reaction vessel.

8. A process for the production of unsaturated hydrocarbons having 2 to 4 carbon atoms by the catalytic hydrogenation of carbon monoxide comprising:
   (a) reducing a catalyst consisting essentially of a carrier of not more that 50% by weight based on the total weight of said catalyst which consists essentially of iron, an oxide of titanium, zinc oxide and potassium oxide wherein the weight ratio of said iron to said titanium is between about 10:1 and 2:1 with hydrogen at a temperature of between about 350° C. and 520° C. and a pressure of about one bar;
   (b) reacting hydrogen and carbon monoxide in the presence of said catalyst in a reaction vessel at a reaction temperature of between about 250° C. and 350° C. and a reaction pressure of between about 10 and 30 bar, whereby said unsaturated hydrocarbons are formed;
   (c) removing said unsaturated hydrocarbons from said reaction vessel;
   (d) recycling the unreacted carbon monoxide and hydrogen;
   (e) removing said catalyst continuously or intermittently from said reaction vessel;
   (f) burning said catalyst in the presence of air whereby impurities are removed;
   (g) reducing said catalyst whereby a regenerated catalyst is formed; and
   (h) returning said regenerated catalyst to said reaction vessel.

9. The process of claim 1 wherein said carrier is selected from the group consisting of synthetic or natural silicic acid, kieselguhr, diatomaceous earth, aluminum oxide, aluminum oxide hydrate, and natural and synthetic silicates.

* * * * *